United States Patent
KrishnaRaj et al.

(10) Patent No.: US 6,313,374 B1
(45) Date of Patent: Nov. 6, 2001

(54) METHOD OF USING PELAROGONIUM SP. AS HYPERACCUMULATORS FOR REMEDIATING CONTAMINATED SOIL

(75) Inventors: Sankaran KrishnaRaj; Praveen K. Saxena, both of Guelph; Michel R. Perras, Kitchener, all of (CA)

(73) Assignee: University of Guelph, Guelph (CA)

( * ) Notice: Subject to any disclaimer, the term of this patent is extended or adjusted under 35 U.S.C. 154(b) by 0 days.

(21) Appl. No.: 09/185,797

(22) Filed: Nov. 4, 1998

Related U.S. Application Data

(60) Provisional application No. 60/064,238, filed on Nov. 4, 1997.
(51) Int. Cl.$^7$ .............................. A01G 1/00; A01H 1/00; A01H 3/00; C12N 15/82
(52) U.S. Cl. ........................... 800/278; 800/294; 47/58.1
(58) Field of Search .................................. 800/278, 294; 47/58.1; 75/711

(56) References Cited

U.S. PATENT DOCUMENTS

| | | | |
|---|---|---|---|
| 4,872,985 | 10/1989 | Dinges | 210/602 |
| 5,120,441 | 6/1992 | Jackson | 210/602 |
| 5,320,663 | 6/1994 | Cunningham | 75/432 |
| 5,364,451 | 11/1994 | Raskin | 75/710 |
| 5,393,426 | 2/1995 | Raskin | 210/602 |
| 5,668,294 | 9/1997 | Meagher | 800/205 |
| 5,917,117 | * | 6/1999 | Ensley et al. | 75/711 |

FOREIGN PATENT DOCUMENTS

| | | | |
|---|---|---|---|
| WO 94/01367 | * | 1/1994 | (WO) | C02F/3/32 |
| WO 97/17429 | | 5/1997 | (WO) | C12N/5/04 |
| WO 97/45000 | | 12/1997 | (WO) | A01H/5/00 |

OTHER PUBLICATIONS

Raskin et al., Bioconcentration of heavy metals by plants. Current Opinion in Biotechnology. 5:285–290, 1994.*
Ananyan et al., Uptake of radioactive and stable elements by plants under conditions of soil and hydroponics. Agrokhimiya. 0(12), 80–84, 1983.*
Romero et al., Metal plant and soil pollution indexes. Water, Air, and Soil Pollution, vol. 34, No. 4. pp 347–352, 1987.*
Richter's Herb Catalogue, pp. 30–33, 1997.*
Sankaran KrishnaRaj, Yong–Mei Bi, Praveen K. Saxena, Somatic embryogenesis and *Agrobacterium*–mediated transformation system for scented geraniums (*Pelargonium* sp. 'Frensham'). Planta, Springer–Verlag 434–440 (1997).
Stephen G. Rogers, Robert B. Horsch, Robert T. Fraley, Gene Transfer in Plants: Production of Transformed Plants using Ti Plasmid Vectors. Methods for plant molecular biology, (1988, Academic Press, Inc.), 423–436.
Rufus L. Chaney, Minnie Malik, Yin M. Li, Sally L. Brown, Eric P. Brewer, J. Scott Angle, Alan J.M. Baker, Phytoremediation of soil metals. Environmental Biotechnology, 8:279–284 (1997).

Ilya Raskin, Robert D. Smith and David E. Salt, Phytoremediation of metals: using plants to remove pollutants from the environment. Plant Biotechnology, 8:221–226 (1997).

P.B.A. Nanda Kumar, Viatcheslav Dushenkov, Harry Motto and Ilya Raskin, Phytoextraction: The Use of Plants to Remove Heavy Metals from Soils. *Environ. Sci. Technol.* 29, 1232–1238 (1995).

Jianwei W. Huang, Jianium Chen, William R. Berti, Scott D. Cunningham, Phytoremediation of Lead–Contaminated Soils: Role of Synthetic Chelates in Lead Phytoextraction. *Environ. Sci. Technol.* 31, 800–805 (1997).

S.L. Brown, R.L. Chaney, J.S. Angle, A.J.M. Baker, Phytoremediation Potential of Thlaspi *caerulescens* and Bladder Campion for Zinc–and Cadmium–Contaminated Soil. J. Environ. Qual. 23:1151–1157 (1994).

David E. Salt, Michael Blaylock, Nanda P.B.A. Kumar, Viatcheslav Dushenkov, Burt D. Ensley, Ilan Chet, Ilya Rasking, Phytoremediation: A Novel Strategy for the Removal of Toxic Metals from the Environment Using Plants. Biotechnology, 13:468–474 (1995).

Michael J. Blaylock et al., Enhanced Accumulation of Pb in Indian Mustard by Soil–Applied Chelating Agents. *Environ. Sci. Technol.*, 31:860–865, 1997.

Scott D. Cunningham, David W. Ow, Promises and Prospects of Phytoremediation. Plant Physiol., 110:715–719 (1996).

* cited by examiner

*Primary Examiner*—Bruce R. Campell
*Assistant Examiner*—Anne Marie Grünberg
(74) *Attorney, Agent, or Firm*—Oppedahl & Larson LLP

(57) ABSTRACT

A process for effectively remediating soils contaminated with individual or mixture of metal ions is described. The process involves utilizing plants of the genus Pelargonium, particularly Pelargonium sp., to hyperaccumulate metal ions in their roots and shoots. These plants when grown on soils, which contain one or more of the metal ions, individually or in a complex mixture, will uptake the metal ions through their roots and translocate them to the shoots. This process thereby removes the metal ions from the soil. The harvested shoot and root biomass can be used for extraction of essential aromatic oils, and the residual oil-extracted biomass will be available for extraction and recycling of the metals. The process also describes the use of the above said plant(s) for remediating land-farming sites of petroleum industries, which are generally contaminated with a mixture of metal ions and organic contaminants. The plant surpasses all the requirements of an ideal hyperaccumulator such as, robust growth habit, large shoot biomass (primarily leaves), effective root system, ability to survive and uptake of a wide array of metal ions, ability to retain senescing plant parts, in addition to potential economic returns in the form of essential aromatic oils from harvestable biomass.

18 Claims, No Drawings

METHOD OF USING PELAROGONIUM SP. AS HYPERACCUMULATORS FOR REMEDIATING CONTAMINATED SOIL

This application is a regular application under 35, USC §111(a) and claims priority from U.S. application Ser. No. 60/064,238, filed Nov. 4, 1997 which is incorporated by reference in its entirety.

BACKGROUND OF THE INVENTION

Domestication of plants for human consumption has resulted in altering most crops and crop-related plant's ability to uptake metals from the soil medium. The ultimate aim of many decades of plant breeding practices has been to reduce the accumulation of unfavourable substances in plant parts that are destined for human or animal consumption. However, a few wild and native plant species have, to date, retained their ability to uptake undesirable toxic substances from the growth medium on which they establish. Some of these plant species often accumulate very high concentrations of metal ions in their foliage. These plants are commonly classified as "hyperaccumulators". Hyperaccumulators are plants which can accumulate toxic metal ions, such as nickel, copper, cobalt and lead at very high concentrations in shoot or root tissues (>0.1% of the dry matter). These plants are normally found growing in soils containing unusually high concentrations of these metals in special geological formations, for example, the presence of zinc accumulating Thlaspi plants growing in zinc-rich soils near the Germany and Belgium border. To date, only a handful of hyperaccumulating plant species have been identified for their potential to uptake different metal species (see Table A.).

The term phytoremediation refers to the effective utilization of such metal-hyperaccumulating plant species which have the ability to uptake, bind, and detoxify environmental contaminants, such as metal ions and organics, through plant-mediated biological, biochemical and physical means. The current focus of researchers is to identify and select better plant species for phytoremediation, species that can be classified as hyperaccumulators and that also possess a large biomass into which the plants can accumulate and sequester large quantities of toxic metal ions. The identified plants must be hardy and suitable for the temperate North American environment. As stated by Brown et al. (1995), the hyperaccumulation mechanism involves the translocation of the metals from soil to shoot tissues in excess of 100 mg/kg for Cadmium, 1,000 mg/kg for Nickel and 10,000 mg/kg for Zinc, Copper and Cobalt hyperaccumulators are defined as plants capable of accumulating more than 0.1% (1,000 mg/kg) of these metals in their dried tissue (Baker et al., 1988).

TABLE A

Metal concentrations in the known hyperaccumulator species [concentration in harvestable material from plants growing in contaminated soils (on dry weight basis)]

| Metal | Plant Species | Concentration [mg/kg in shoots] |
|---|---|---|
| Cd | Thlaspi caerulescens | 1,800 |
| Cu | Ipomea alpina | 12,300 |
| Co | Haumaniastrum robertii | 10,200 |
| Pb | T. rotundzfoliium | 8,200 |
| Mn | Macademia neurophylla | 51,800 |

TABLE A-continued

Metal concentrations in the known hyperaccumulator species [concentration in harvestable material from plants growing in contaminated soils (on dry weight basis)]

| Metal | Plant Species | Concentration [mg/kg in shoots] |
|---|---|---|
| Ni | Psychotria douarrei | 47,500 |
|    | Sebertia acuminata | (25% by wt of dried sap) |
| Zn | T. caerulescens | 51,600 |

The major limitations of utilizing these hyperaccumulating plant species for phytoremediation are:
a) Plants such as Thlaspi and Haumaniastrum are very small, with a very low plant biomass. Although these plants can uptake metals >1% of their dry weight ("DW"), their low biomass limits their ability to uptake large amounts of metal ions. For example, shoots of T. rotundifolium can accumulate up to 8200 mg/kg DW of Pb but these plants can only produce 5 to 50 mg of plant dry material during a 5 month growing period. Therefore, these plants would have to be grown over several growth cycles and seasons in order to achieve complete remediation of a site.
b) Plants such as Thlaspi and Haumaniastrum are very small in stature, and therefore are not amenable for harvesting using conventional farm machinery.
c) Plants such as Thlaspi and Haumaniastrum have a very slow growth habit (Thlaspi rotundifolium has a 5 month growth period). A long growth cycle would result in longer remediation periods.
d) Tree species such as Sebertia acuminata have a longer growth period but due to their tropical origin, they might not be able to over-winter in temperate environments, and hence may not be useful for phytoremediation purposes in North America.
e) All the hyperaccumulator plant species mentioned above have specific target metal species, which they are capable of accumulating in very large amounts in their plant parts. However, most of the contaminated soil sites have a mixture of metal contaminants. In the presence of such complex metal contaminants, it is very unlikely that these known hyperaccumulators will be able to survive and uptake large levels of the different metal ions. For example, petroleum industries land-farming sites in Sarnia, Ontario, Canada, have a mixture of about 15 different metal ions and organic contaminants in varying concentrations, depending on the location.

Among the hyperaccumulating plant species currently being considered for phytoremediation and which have been characterized in greenhouse and field conditions, the most promising ones are Thlaspi caerulescens and plants belonging to the Brassicaceae family.

The limitation of using plants belonging to the Brassicaceae family are:
a) Most of the currently identified plants are wild relatives of the cultivated crop species Brassica napus (canola). Due to the potential for cross-pollination between the wild-relatives and crop species, public acceptance of these plants for phytoremediation is questionable. This problem holds credence considering the potential for evolution of new weed-like species, which might interfere with current agricultural systems.
b) These plants set seeds readily and might assume weed-like characteristics after repeated growth in contaminated sites.
c) These plants have relatively larger biomass than Thlaspi sp. However, they still do not compare well with plants with denser foliage (larger biomass).

The ability of plants to extract metal ions from soils and accumulate or sequester those metals in their tissues can be tremendously improved by adjusting the pH of the soil and also by the addition of synthetic chelators to the growing media. These two elements increase the release (desorption) of metal ions from soil particles, thereby increasing the availability of those ions to the plant roots, resulting in increased rate of uptake. The limitations of using metal chelators are:

The addition of chelating agents to metal contaminated soils could bring in new problems regarding health, safety and environmental concerns. Addition of large amounts of chelates will result in rapid solubilization of different metal ions. Some of the metals released will be beneficial to plants and microflora of the soil. However, this will also increase the soil solution concentration of undesirable ions. Moreover, there is a larger risk of releasing large amounts of the solubilized toxic metals in the underground water systems. The use of chelates would increase the bioavailability and uptake of these toxic metals by the natural flora and fauna of the soil, thereby accelerating the spread of these metals in the ecosystems and in the different food chains.

SUMMARY OF THE INVENTION

The present invention provides a process for remediating a growth medium contaminated with metal ions. More specifically, this invention provides a process for remediating a growth medium contaminated with metal ions using Pelargonium sp. plants.

According to one aspect of the invention, there is provided a method for removing one or more species of metal from a metal contaminated growth medium, comprising growing a Pelargonium sp. plant in the growth medium for a time period sufficient for the plant root to uptake and accumulate metal in the root or shoot biomass.

In a further aspect of the invention, the method for removing one or more species of metal from a metal contaminated growth medium further comprises the extraction of essential aromatic oils or concentration of metals from the root or shoot biomass.

In another of its aspects, the invention provides a method for removing one or more species of metal from a growth medium (the growth medium is preferably metal contaminated) which comprises growing a Pelargonium sp. plant, which has been transformed with a gene sequence encoding for a desirable trait, in the growth medium for a time period sufficient for the plant root to uptake and accumulate metal in the root or shoot biomass.

These and other embodiments of the present invention are described in greater detail hereinbelow.

DETAILED DESCRIPTION OF THE INVENTION

Contamination of cultivable lands with toxic levels of metal ions poses an environmental risk to humans, animals and agriculture. Remediation of such contaminated soils through conventional practices (such as solidification or stabilization techniques, soil flushing, bioremediation, electrokinetics, chemical reduction and oxidation, soil washing, pneumatic fracturing, as well as the process of excavation, retrieval, and off-site disposal) are often expensive, have limited performance potential and are applicable only to small areas. The developed alternative process of the invention is a low-cost phytoremediation system for clean-up of metal-tainted soils using plant species that can hyperaccumulate a wide variety of metal ions. Phytoremediation refers to the effective utilization of certain metal-hyperaccumulating plant species to uptake, bind, and detoxify environmental contaminants, such as metal ions and organics, through plant-mediated biological, biochemical and physical means. Phytoremediation technology also possesses an added advantage because the sites after remediation utilizing this process are still agriculturally viable, while those remediated through conventional practices are often sterile, as most essential nutrients are stripped-off from the soil.

To date there are only a handful of known hyperaccumulating species. Based on our studies we have identified a plant species, scented geranium (Pelargonium sp.) which has shown tremendous potential as an hyperaccumulator of several heavy metal ions.

The successful use of scented geraniums as hyperaccumulators in phytoremediation was unexpected in view of the research by others in this area. To date, all known hyperaccumulators are seed-propagated. Seed-propagation of the hyperaccumulators allows for ease in seeding the plants in contaminated sites. There are no known hyperaccumulators which are vegetatively (cutting) propagated. Most researchers working in this area, have so far and are still, focusing on identifying hyperaccumulating seed-propagated plants but have never attempted to identify hyperaccumulating vegetatively propagated plants.

Also, most efforts at identifying hyperaccumulators have focused on identifying and selecting plant species which naturally grow in metal enriched soils, while not much effort was made in recognizing the hyperaccumulating potential of domesticated, economically important, non-food crops/plants. Scented geranium is one such plant species, which is known world-wide for its ornamental characteristics, but has never been considered for its potential in phytoremediation.

Scented geranium plants grow well in a wide variety of growth media ranging from artificial soil mix (peat, perlite, vermiculite combinations), sand, to petroleum industries land-farming sites which contain mixtures of metal ions and organics. These plants are very hardy and can withstand a wide range of temperature, humidity, photoperiod and watering schedules. These plants are not season-dependent and can be grown and harvested several times during a calendar year. The time required for these plants to uptake metal ions is relatively short (uptake data is based on just a 2 week treatment period) and therefore several cycles can be accommodated in one growing season. These plants are propagated by cuttings and rarely flower, so there is no potential out-crossing, and they do not assume weed-like characteristics. Due to the pleasant but intense lemon-scented leaves with numerous trichomes, these plants are less susceptible to pest outbreak or herbivore damage. The plant has an aesthetic value, and a commercial significance (essential aromatic oils in the biomass) thereby it should promote public acceptance of the technology. The advantages of the process of utilizing plants belonging to the genus Pelargonium as candidate plants for phytoremediation are (in comparison to other hyperaccumulator species known to date):

a) The plants (belonging to the genus Pelargonium, especially Pelargonium sp. 'Frensham', Pelargonium sp. 'Citrosa' and Pelargonium sp. 'Beauty Oak') ability to survive on soils contaminated with one or more metal ions. Most known hyperaccumulators have limited potential in phytoremediation, as they are suitable for remediating only specific (individual) metals.

b) The plants' (belonging to the genus Pelargonium, especially Pelargonium sp. 'Frensham', Pelargonium sp. 'Citrosa' and Pelargonium sp. 'Beauty Oak') ability to uptake, translocate and accumulate a wide array of metal ions, such as cadmium, lead, zinc, copper, nickel in the shoot biomass. Most known hyperaccumulators can uptake only one specific metal ion, and therefore are limited in their applicability to remediate soils with complex metal ion mixtures.

c) The plants (belonging to the genus Pelargonium, especially Pelargonium sp. 'Frensham', Pelargonium sp. 'Citrosa' and Pelargonium sp. 'Beauty Oak') possess a very dense foliage (consisting mostly of leaves) for sequestering high levels of metal ions in the above ground parts. The shoot biomass is exceptionally higher than any known hyperaccumulator e.g., Thlaspi sp., and plants belonging to Brassicaceae family.

d) The plants (belonging to the genus Pelargonium, especially Pelargonium sp. 'Frensham', Pelargonium sp. 'Citrosa' and Pelargonium sp. 'Beauty Oak') have a faster and robust growth habit. Most known hyperaccumulators (e.g., Thlaspi sp.) have a very slow growth habit. Pelargonium sp. 'Frensham' can attain a biomass of greater than 4 kg within 5–6 month growth period.

e) The plants (belonging to the genus Pelargonium, especially Pelargonium sp. 'Frensham', Pelargonium sp. 'Citrosa' and Pelargonium sp. 'Beauty Oak') have an efficient and prolific root system that can efficiently absorb metal ions from the soil or ground water. Pelargonium sp. has a prolific root system, which can grow up to 3–4 feet within a 5–6 month growth period.

f) The plants (belonging to the genus Pelargonium, especially Pelargonium sp. 'Frensham', Pelargonium sp. 'Citrosa' and Pelargonium sp. 'Beauty Oak') have the ability to grow in a wide variety of soils with relatively low requirements for water, nutrients and other conditions required to sustain growth and metabolism (they are also viable in different types of soil, soil factors, and in adverse environments unlike many other known hyperaccumulators).

g) The plants (especially Pelargonium sp. 'Frensham', Pelargonium sp. 'Citrosa' and Pelargonium sp. 'Beauty Oak') have the ability to moderately retain senescing and dead leaves (without withering) thereby reducing recycling of metal ions to the contaminated soil, (a very distinct characteristic of certain scented geraniums).

h) The use of harvested plants (especially Pelargonium sp. 'Frensham', Pelargonium sp. 'Citrosa' and Pelargonium sp. 'Beauty Oak' shoot biomass) for extraction of essential aromatic oils such as, citronellol, geraniol, isomethane, geranyl formate etc. No other hyperaccumulator has been shown to have economic return from plants used for phytoremediation.

It is an aspect of the present invention to provide a method for removing one or more species of metal (such as metal in an ionic form, elemental form or organometalic form) from a metal contaminated growth medium, comprising growing a Pelargonium sp. plant in the growth medium for a time period sufficient for the plant root to uptake and accumulate metal in the root or shoot biomass. In a specific embodiment of the invention, the plant is selected from Pelargonium sp. 'Frensham', Pelargonium sp. 'Citrosa' and Pelargonium sp. 'Beauty Oak'. In a more specific embodiment, the plant is selected from Pelargonium sp. Frensham and Pelargonium sp. 'Beauty Oak'. In the most specific embodiment, the plant is Pelargonium sp. 'Frensham'. Other varieties of Pelargonium sp. are also useful as hyperaccumulators. A partial list of Pelargonium sp. is provided in Table 7. One of ordinary skill in the art can measure the ability of these plants and other Pelargonium sp. to hyperaccumulate metals using the methods described in this application.

In another embodiment of the invention, the growth medium comprises solid medium, semi-solid medium, liquid medium (preferably a hydroponic growth medium) or a combination thereof. In a preferred embodiment, the growth medium comprises soil, sand, sludge, compost or artificial soil mix. In another embodiment of the invention, the growth medium comprises soil, sand, sludge, compost or artificial soil mix which further comprises organic contaminants. The growth medium may also comprise waste water or waste compounds. In specific embodiments, these organic contaminants are selected from the group consisting of petroleum industry by-products and petroleum industry wastes.

In another embodiment of the present invention, the species of metal to be removed from the contaminated growth medium is any metal likely to be found in metal-contaminated growth medium. In specific embodiments, the metal species in selected from one or more of the group consisting of lead, cadmium, copper, nickel, zinc, antimony, boron, vanadium, chromium, cobalt, manganese, selenium, arsenic, molybdenum, beryllium, barium, mercury, silver, antimony, titanium, thallium, tin, gold, rubidium, strontium, yttrium, technicium, ruthenium, palladium, indium, cesium, uranium, plutonium and cerium. In more specific embodiments, the metal is selected from the group consisting of one or more of the group consisting of lead, cadmium, copper, nickel and zinc. The method is used to remove metal from growth media containing one metal in large quantity or a combination of metals in a variety of concentrations. When the metal contaminate comprises cadmium, it is an embodiment of the invention that the concentration of cadmium accumulated is in the range of about 200 mg Cd/kg to 30,000 mg Cd/kg (preferably 450 mg Cd/kg to 27,500 mg Cd/kg) dry weight of the plant. When the metal contaminate comprises lead, it is an embodiment of the invention that the concentration of lead accumulated is in the range of 1000 mg Pb/kg to 70,000 mg Pb/kg (preferably 1,300 mg Pb/kg to 66,000 mg Pb/kg) dry weight of the plant. When the metal contaminate comprises copper, it is an embodiment of the invention that the concentration of cadmium accumulated is in the range of about 200 mg Cu/kg to 1,000 mg Cu/kg (preferably 230 mg Cu/kg to 620 mg Cu/kg) dry weight of the plant. When the metal contaminate comprises nickel, it is an embodiment of the invention that the concentration of nickel accumulated is in the range of about 200 mg Ni/kg to 25,000 mg Ni/kg (preferably 400 mg Ni/kg to 21,500 mg Ni/kg) dry weight of the plant.

It is another aspect of the present invention that the method further comprises the step of harvesting one or more parts of the plant selected from the shoot and root biomass. In a specific embodiment, when the shoot biomass is harvested, the shoot biomass comprises a leaf or a stem. In another specific embodiment, when the shoot biomass is harvested, a sufficient portion of the shoot biomass is not harvested to permit continued growth of the plant. It is another embodiment of the present invention that the method further comprises the step of harvesting one or more parts of the plant selected from the shoot and root biomass and extracting essential aromatic oil from said biomass. In specific embodiments, the essential aromatic oil is obtained by distillation. In more specific embodiments, the essential aromatic oil is selected from citronellol, geraniol, isomethane and geranyl formate. Also, it is another embodiment of the present invention that the method further comprises the step of harvesting one or more parts of the plant selected from the shoot and root biomass and concentrating the metal using any known method for concentrating metals from plant biomass. Specifically, the concentration of the metal may be carried out by air drying, dehydrating, ashing, incineration, smelting, aerobic digestion or anaerobic digestion of the residual oil-extracted shoot biomass.

It is another aspect of the present invention that the method for removing one or more species of metal from a metal contaminated growth medium further comprises growing a Pelargonium sp. plant which has been transformed with a gene sequence encoding for a desirable trait. In an embodiment of the invention the Pelargonium sp. plant is transformed with a gene sequence that enhances the plants' ability to uptake metals. In a specific embodiment of the invention, the Pelargonium sp. plant is transformed with a gene sequence encoding metallothionein. In another specific embodiment of the invention, the Pelargonium sp. plant is transformed with a gene sequence encoding phytochelatin synthase. It is another emdodiment that the Pelargonium sp. plant is transformed by the introduction of genes through delivery vehicles such as particle bombardment or Agrobacterium vectors or using techniques such as microinjection and electroporation. In a specific emdodiment, the Pelargonium sp. plant is transformed by an Agrobacterium strain.

We assess the hyperaccumulation of Pelargonium sp. plants. The ability of the plants to uptake different metal ions is investigated by adding different concentrations of each metal ion to the growth medium, and estimating the metal content in harvested roots and shoots. The concentration of the metal ions is increased with each experiment in order to identify the LD50 (concentration at which 50% of the plants exhibit physiological senescence and death) dose (for the set 2-week treatment period). This experiment identifies the maximum threshold of metal concentration in which the plant can survive and perform remediation processes.

Scented geranium plants are grown on a growth medium containing a mixture of heavy metals and we assess the plants ability to uptake simultaneously a wide array of metal ions present. This study provides the interaction effects of the different metal ions and how they are selectively taken up by the plant. Other scented geranium plant species along with plants belonging to the Pelargonium sp. are grown on similar growth medium containing metal ions either individually or in complex combinations and we assess these plants' ability to uptake, and translocate metal ions to the shoots. These plants are harvested and used in isolation of essential aromatic oil or concentration of metals. In a preferred variation, the invention relates to a method of obtaining one or more metals from a growth medium.

Plants belonging to the Pelargonium sp. are also grown on soils of land-farming sites (for example land-farming sites), and other contaminated sites (either in the greenhouse or by direct planting on the site), to show the ability of the said plant to uptake metals from a complex soil medium containing metals as well as organic contaminants.

A preferred mode of utilizing scented geraniums (or plant belonging to the Pelargonium sp.) is to plant well-rooted cuttings (1 month old cuttings) in soil (artificial soil mix, soil) which contains one or more of the heavy metal ions. The plants are irrigated biweekly with regular tap water (approximate pH range of water being 5–9). The plants do not need fertilization if a two-week treatment schedule is followed. Otherwise, plants can be fertilized as required. The plants require natural sunlight and normal temperature regimes to perform essential metabolic activities. The plants should be grown (for a minimum) of 2 weeks in the growth medium to allow the plant to uptake metal ions and translocate them to the shoots. The metal-laden shoot and root biomass, after the two-week or other pre-determined treatment period, can be harvested manually or mechanically. The plant material (if left behind after harvest of shoots) can be allowed to grow back in the next cycle, or new cuttings can be planted in the same site. The biomass can be extracted to obtain essential aromatic oils and the oil-extracted biomass can be used for metal extraction and recycling or disposal. These procedures can be varied by one skilled in the art using known techniques in order to use scented geraniums in other soil types. The geraniums may also be grown from seeds or other cuttings or plant parts, as known in the art.

The described process of using plants of the Pelargonium sp. for phytoremediation will have commercial application in remediating contaminated sites such as those identified by: a) the National Priorities List (Superfund sites), b) Resource Conservation and Recovery Act (RCRA) Corrective Action sites, c) Underground Storage Tank sites, d) Department of Defense sites, e) Department of Energy sites, as well as f) other federal, provincial, state and private party-owned sites. The primary application will be to cleanup contaminated sites associated with abandoned mines, abandoned tailing sites, petroleum industries waste disposal sites inclusive of land-farming sites, explosives and unexploded ordinance storage and dump sites, sewage sludge dump sites, radioactive and industrial waste-treatment and disposal sites.

Pelargonium sp. plants, or mutants of the plant, developed by mutagenesis with chemical mutagens such as EMS, MMS, ENU, or physical mutagens such as X-ray, gamma-rays; or somaclonal or gametoclonal variants of the said plant(s) selected and developed through tissue culture procedures, spontaneously or induced by mutagens are used in phytoremediation. These variants and other variants of Pelargonium sp. that may be used as hyperaccumulators are within the scope of the invention.

Microorganisms, such as Pseudomonas sp., which enhance plant growth or metal availability (through chelating action) may be used by co-habiting with roots in the rhizosphere. The choice of suitable organisms is made according to considerations known in the art.

Soil chemistry can be regulated to facilitate plant growth, availability of metals (such as entrapped metals) or metal uptake. The plants' hyperaccumulating ability to uptake and sequester large amounts of metal ions can be enhanced by use of soil treatments or chemicals that make metals in soils more available to the roots of plants, such as metal chelating agents. To enhance the scented geranium plants ability to uptake metal ions from the growth medium, we are utilizing metal-chelating agents such as EDTA, HEDTA, EGTA, DTPA, etc. in the growth medium. Any other suitable chelating agent may also be used in the methods of this invention. These metal chelators solubilize the metal ions and make them easily available to the roots for easy uptake. Among the chelating agents, EGTA and EDTA have been found to be the most effective chelators at enhancing the accumulation of metal by the plants. EDTA is about 10–times less expensive than EGTA, which makes it more attractive for extensive commercial applications in large contaminated sites. We have also modified the pH of the growth medium and determined the effect of pH on the bioavailability of the different metal species. The interaction of pH and chelating agents on bioavailability of metals and the scented geranium plants ability to uptake those metal ions has been investigated.

Genetic transformation technology is used to transform the plant with genes such as the metallothionein gene or phytochelatin synthase gene to enhance uptake and effectively bind metal in the shoot, through use of site specific promoters. When expressed throughout the plant, the polypeptides produced by these genes bind metals in the root or in the shoot. The polypeptide-metal complex is sequestered in the vacuoles of cells. Sequestration prevents the accumulated metal from interfering with metabolism. The complex cannot be translocated within the plant. If the polypeptide is expressed in the root, one must harvest the whole plant to gather all of the polypeptide-metal complexes. Preferably the gene is expressed specifically in the shoot so that only the shoot is harvested in order to gather the polypeptide-metal complexes. The remaining plant will then continue to grow and uptake more metal from the contaminated soil.

High frequency regeneration and Agrobacterium-mediated transformation systems are used to obtain stably transformed scented geraniums containing gene(s) encoding for metallothionein or phytochelatin synthase. The plants may also be transformed with other genes to enhance uptake of metals.

The invention also relates to Pelargonium sp. cells, tissue cultures, plants, seeds or plant parts (such as roots, shoots or cuttings) transformed with recombinant metallothionein gene or phytochelatin synthase gene or a gene that is biologically functional equivalent to the metallothionein gene or the phytochelatin synthase gene and their use in phytoremediation. The invention also relates to methods of making Pelargonium sp. including a recombinant metallothionein gene or a phytochelatin synthase gene or a biologically functional equivalent gene, by inserting at least one of the aforementioned genes into a Pelargoniium sp. cell, tissue culture, plant, seed or plant part. In the preferred embodiment, a plant is generated from the cell, tissue culture, seed or plant part.

Biologically functional equivalent nucleotide sequences are DNA and RNA (such as genomic DNA, cDNA, synthetic DNA, and mRNA nucleotide sequences), that encode peptides, polypeptides, and proteins having the same or similar activity as the proteins encoded by the metallothionein gene or the phytochelatin synthase gene. Biologically functional equivalent nucleotide sequences can encode peptides, polypeptides, and proteins that contain a region having sequence identity to a region of a metallothionein gene or a phytochelatin synthase gene.

The invention includes Pelargonium sp. transformed with biologically functional equivalent nucleotide sequences that encode conservative amino acid changes within an amino acid sequence produced by the metallothionein gene or the phytochelatin synthase gene and which produce silent amino acid changes.

The invention includes Pelargonium sp. transformed with nucleotide sequences that are biologically functional equivalent to the metallothionein gene or the phytochelatin synthase gene which encode peptides, polypeptides, and proteins having non-conservative amino acid substitutions, additions, or deletions but which also retain the same or similar activity as metallothionein gene or the phytochelatin synthase gene. The DNA or RNA can encode fragments or variants of metallothionein gene or the phytochelatin synthase gene. The metallothionein gene or the phytochelatin synthase gene activity of such fragments and variants is identified by assays as known in the art. One skilled in the art could take a fragment including the nucleic acid sequence of the coding region of the gene (or a biologically functional equivalent gene) and insert it in an expression vector. Fragments and variants of the metallothionein gene or the phytochelatin synthase gene encompassed by the present invention should preferably have at least about 40% sequence identity or preferably at least about 60%, at least about 80%, at least about 90% or at least about 95% sequence identity to the naturally occurring gene, or corresponding region or moiety. Most preferably, the fragments have at least 97%, 98% or 99% sequence identity to the naturally occurring gene, or corresponding region. Sequence identity is preferably measured with either the Gap or BestFit programs. BestFit aligns the best segment of similarity between two sequences. Alignments are made using the local homology algorithm of Smith and Waterman (1981) Adv. Appl. Math. 2:482–489. The algorithm of Needleman and Wunsch (1970 J Mol. Biol. 48:443–453) is used in the Gap program.

In the case of a recombinant gene, the gene would contain suitable transcriptional or translational regulatory elements. Suitable regulatory elements may be derived from a variety of sources, and they may be readily selected by one with ordinary skill in the art. If one were to upregulate the expression of the gene, one would insert the sense sequence and the appropriate promoter into the vehicle. If one were to downregulate the expression of the gene, one would insert the antisense sequence and the appropriate promoter into the vehicle. Genetic engineering and manipulation of plants is described in Rogers et al., 1988 (Gene Transfer in plants: Production of transformed plants using Ti plasmid vectors, *Methods for Plant Molecular Biology*). Other techniques for genetic engineering are known to those skilled in the art.

Examples of regulatory elements include: a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecules. The recombinant molecules may be introduced into cells of a Pelargonium sp. using delivery vehicles such as particle bombardment or using Agrobacterium vectors. They may also be introduced into such cells using physical techniques such as microinjection and electroporation.

An Agrobacterium-mediated transformation system may be used to transform Scented geraniums at high frequency (Rogers et al., 1988). The same method will apply to introduce new recombinant metallothionein or phytochelatin synthase genes into geranium plants or cells to obtain transgenic plants with greater heavy-metal accumulating potential. The constructs used to transform the plants preferably contain site-specific promoters. These promoters can regulate and limit the expression of the new genes to specifically targeted tissues. In the phytoremediation context, it is important to increase the capacity of uptake and sequestration of the absorbed metal to the above ground plant parts thereby facilitating its harvest.

We use procedures and protocols for obtaining transformed cells and subsequently obtaining transformed plants using regeneration systems (through somatic embryogenesis). An efficient and reliable regeneration system (through somatic embryogenesis) is also available for mass propagation of the said plant. Techniques for somatic embryogenesis are described in KrishnaRaj et al., 1997 (Somatic embryogenesis and Agrobacterium-mediated transformation system for scented geraniums (Pelargonium sp. 'Frensham'), *Planta*, 201: 434–440; 1997). The effectiveness of the developed regeneration and transformation system was also successfully demonstrated by using the system to incorporate genes which impart resistance to Botrytis infection into scented geraniums, Pelargonium sp.

'Frensham' (Bi et al., 1998, Resistance to *Botrytis cinerea* infection in scented geraniums by incorporating a gene Ace-AMPI encoding for an antimicrobial protein, Plant Cell Reports, in press).

Another aspect of the invention relates to a method of determining whether a test vegetative (cutting) propagated plant is a hyperaccumlator of one or more compounds by growing the test plant in a growth medium including at least one compound (preferably at least one of the metals described in this application which is present in higher concentration than the metal is typically present in the growth medium) and determining whether the plant hyper-accumulates the compound.

The invention also includes the use of a vegatative (cutting) propagated plant as a hyperaccumulator of metal in a growth medium. In another variation, the invention includes a method for removing one or more species of metal from a growth medium comprising growing a vegetative (cutting) propagated plant in the growth medium for a time period sufficient for the plant root to uptake and accumulate metal (preferably in the root or shoot biomass). In the preferred embodiment of the method, the growth medium is metal contaminated.

The Pelargonium sp. can also be planted with hyperaccumulators known in the art and used together in methods of the invention. One skilled in the art could vary growing conditions to optimize growth of more than one type of hyperaccumulator.

EXPERIMENT 1
Scented Geranium Plants and Cadmium Uptake (Low Cd Concentrations)

Three separate experiments were conducted with replicate cutting propagated plants of scented geraniums to assess their ability to uptake and sequester cadmium in the shoots and roots. In the first experiment, 2 concentration levels of cadmium (Cd1 and Cd2) were selected for treating the scented geraniums [0.6 mg (Cd1) and 2.5 mg (Cd2) of cadmium nitrate dissolved in 250 mL of water per plant; treatments with these concentrations repeated 5 times over a 2 week period; replicate plants were used for each treatment; overall cadmium nitrate fed to each plant being 3 mg (Cd1) and 12.5 mg (Cd2)]. In the second experiment, 2 concentration levels of cadmium (Cd3 and Cd4) were selected for treating the scented geraniums [0.8 mg (Cd3) and 4.2 mg (Cd4) of cadmium nitrate dissolved in 250 mL of water per plant, treatments with these concentrations repeated 4 times in a 2 week period; replicate plants were used for each treatment; overall cadmium nitrate fed to each plant being 3.3 mg (Cd3) and 16.67 mg (Cd4)]. Experiment III was similar to Experiment II except that the plants were watered with alkaline tap water (pH 10.0). In all experiments the plants were harvested after 2 weeks, roots and shoots separated, and dried. Sample preparation consisted of digestion of a known amount of sample in aqua-regia (in both ashed or non-ashed, dried samples), removal of residue by filtration and making up the volume of the filtrate. The samples were analyzed and verified for the concentration of lead by Inductively Coupled Plasma-Emission Spectroscopy (ICP-ES) at Chemisar Laboratories Inc., Guelph, Ontario, Canada and using a Varian Spectra AA-55 Atomic Absorption Spectrophotometer in our laboratory. The data is presented below in Table 1.

EXPERIMENT 2
Scented Geranium Plants and Lead Uptake (Low Pb Concentrations)

Two separate experiments were conducted with replicate cutting propagated plants of scented geraniums to assess their ability to uptake and sequester lead in the shoots. In the first experiment, 2 concentration levels of lead (Pb1 and Pb2) were selected for treating the scented geraniums [6.3 mg (Pb1) and 25 mg (Pb2) of lead nitrate dissolved in 250 mL of water per plant; treatments with these concentrations repeated 5 times in a 2 week period; replicate plants were used for each treatment; overall lead nitrate fed to each plant being 31.5 mg (Pb1) and 125 mg (Pb2)]. In the second experiment, 2 concentration levels of lead (Pb3 and Pb4) were selected for treating the scented geraniums [8.3 mg (Pb3) and 41.7 mg (Pb4) of lead nitrate dissolved in 250 mL of water per plant, treatments with these concentrations repeated 4 times over a 2 week period; replicate plants were used for each treatment; overall lead nitrate fed to each plant being 33.3 mg (Pb3) and 166.7 mg (Pb4)]. Experiment III was similar to Experiment II except that the plants were watered with alkaline tap water (pH 10.0). In all experiments the plants were harvested after 2 weeks, shoots separated, and dried. Sample preparation consisted of digestion of a known amount of sample in aquaregia (in both ashed or non-ashed, dried samples), removal of residue by filtration and making up the volume of the filtrate. The samples were analyzed and verified for the concentration of lead by Inductively Coupled Plasma-Emission Spectroscopy (ICP-ES) at Chemisar Laboratories Inc., Guelph, Ontario, Canada and using a Varian Spectra AA55 Atomic Absorption Spectrophotometer in our laboratory. The data is presented below in Table 1.

Based on the results from Experiments 1 and 2 (data presented in Table 1), we have observed that Frensham scented geranium plants uptake and accumulate greater than 450 mg cadmium, and 1,300 mg lead per kg dry weight of shoot, as well as approximately 10 times higher levels of cadmium (than the shoots) in their roots. Plant species that can accumulate greater than 100 mg Cd/kg dry weight of shoot biomass are classified as hyperaccumulators of cadmium (Brown et al., 1994; Journal of Environmental Quality, 23:1151–1157, 1994; and references therein). Similar experiments were also conducted with nickel and copper and we have so far found that scented geraniums can accumulate greater than 230 mg Cu/kg and 400 mg Ni/kg of dry weight of shoot tissue (results summarized in Table 1)

TABLE 1

Metal accumulation in shoots and roots of scented geranium (Pelargonium sp.) 'Frensham' plants treated with different concentrations of cadmium, lead, copper and nickel in nitrate form. The data points represent mean values of 2 replicate plants in expt. I and 3 replicate plants in expt. II & III). Conc. (mg/l) refer to treatment of plants with the described concentrations during 14 day period.
Uptake (mg/kg DW of tissue)

| Heavy metal | Conc. [mg/l] | Exp I | Heavy metal | Conc. [mg/l] | Exp II | Exp III | Average |
|---|---|---|---|---|---|---|---|
| Shoots | | | | | | | |
| CTL | | 0.0 | | | 0.0 | | |
| CTL | | 0.0 | | | 0.0 | | |
| Cd 1 | 5.0 | 16.7 | Cd3 | 10.0 | 81.0 | — | 57.2 |
| Cd 2 | 20.0 | 97.0 | Cd4 | 50.0 | 459.5 | — | 375.6 |
| Pb 1 | 50.0 | 34.5 | Pb3 | 100.0 | 152.5 | 15.2 | 67.4 |
| Pb 2 | 200.0 | 358.0 | Pb4 | 500.0 | 1306.9 | 501.6 | 722.2 |
| Ni 1 | 20.0 | 37.6 | | 40.0 | 156.0 | 70.7 | 96.8 |
| Ni 2 | 100.0 | 108.3 | | 200.0 | 401.1 | 96.9 | 254.7 |
| Cu 1 | 5.0 | — | | 20.0 | 32.4 | 17.0 | |
| Cu 2 | 20.0 | 18.8 | | 100.0 | 229.7 | 13.6 | |

TABLE 1-continued

Metal accumulation in shoots and roots of scented geranium (Pelargonium sp.) 'Frensham' plants treated with different concentrations of cadmium, lead, copper and nickel in nitrate form. The data points represent mean values of 2 replicate plants in expt. I and 3 replicate plants in expt. II & III). Conc. (mg/l) refer to treatment of plants with the described concentrations during 14 day period.
Uptake (mg/kg DW of tissue)

| Heavy metal | Conc. [mg/l] | Exp I | Heavy metal | Conc. [mg/l] | Exp II | Exp III | Average |
|---|---|---|---|---|---|---|---|
| Root | | | | | | | |
| Cd 1 | | 542.9 | Cd3 | 10.0 | | | 28.2 |
| Cd 2 | | 3220.0 | Cd4 | 50.0 | | | 1987.2 |
| Pb 1 | | | Pb3 | 100.0 | | | 2202.4 |
| Pb 2 | | | Pb4 | 500.0 | | | 18777.0 |
| Ni 1 | | | | 40.0 | | | 267.6 |
| Ni 2 | | | | 200.0 | | | 1576.5 |
| Cu 1 | | | | 20.0 | | | 236.7 |
| Cu 2 | | | | 100.0 | | | 621.2 |

EXPERIMENT 3

Scented Geranium Plants and Cadmium Uptake (High Cd Concentrations)

Two separate experiments were conducted with replicate cutting propagated plants of geraniums to assess their ability to uptake and sequester cadmium in the shoots and roots. Five levels of cadmium were selected for treating the scented geranium [6.25 mg (Cd 5), 12.5 mg (Cd 6), 18.75 mg (Cd 7) 25 mg (Cd 8) of cadmium nitrate dissolved in 50 mL water per plant the treatments with these concentrations were repeated daily over a 2 week period; replicates plants were used for each treatment; overall cadmium nitrate fed to each plant being 87.5 mg (Cd 5), 170 mg (Cd 6), 262.5mg (Cd 7) and 300 mg (Cd 8)]. In both experiments the plants were watered with neutral water (pH 7.0). The plants were harvested after 2 weeks; roots and shoots separated, and dried. Sample preparation consisted of digestion of a known amount of sample using a closed teflon vessel method (Topper, 1990). The samples were analyzed using a Varian Spectra AA Atomic Absorption Spectrophotometer in our laboratory. The data is presented below in Table 2.

EXPERIMENT 4

Scented Geranium Plants and Lead Uptake (High Pb Concentrations)

Two separate experiments were conducted with replicate cutting propagated plants of geraniums to assess their ability to uptake and sequester lead in the shoots and roots. Five levels of lead were selected for treating the scented geranium [25 mg (Pb 5), 37.5 mg (P6), 50 (Pb 7), 62.5 (Pb 8) of lead nitrate dissolved in 50 mL water per plant; treatments with these concentrations were repeated daily over a 2 week period; replicates plants were used for each treatment; overall lead nitrate fed to each plant being 350 (Pb5), 525 mg (Pb 6), 1162 mg (Pb 7) and 875 mg (Pb 8)]. In both experiments the plants were watered with neutral water (pH 7.0). The plants were harvested after 2 weeks; roots and shoots separated, and dried. Sample preparation consisted of digestion of a known amount of sample following a closed teflon vessel method (Topper, 1990). The samples were analyzed using a Varian Spectra AA Atomic Absorption Spectrophotometer in our laboratory. The data is presented below in Table 2.

EXPERIMENT 5

Scented Geranium Plants and Nickel Uptake (High Ni Concentrations)

Two separate experiments were conducted with replicate cutting propagated plants of geraniums to assess their ability to uptake and sequester nickel in the shoots and roots. Five levels of nickel were selected for treating the scented geranium [6.25 mg (Ni 5), 12.5 mg (Ni 6), 18.75 mg (Ni 7) 25 (Ni 8) of nickel nitrate dissolved in 50 mL water per plant; treatments with these concentrations were repeated daily over a 2 week period; replicate plants were used for each treatment; overall nickel nitrate fed to each plant being 87.5 mg (Ni 5), 170 mg (Ni 6), 262.5 mg (Ni 7) and 350 mg (Ni 8)]. In both experiments the plants were watered with neutral water (pH 7.0). The plants were harvested after 2 weeks; roots and shoots separated, and dried. Sample preparation consisted of digestion of a known amount of sample following a closed teflon vessel method (Topper, 1990). The samples were analyzed using a Varian Spectra AA Atomic Absorption Spectrophotometer in our laboratory. The data is presented in Table 2.

Based on the results from Experiments 3–5 (data presented in Table 2), we have observed that Frensham scented geranium plants can uptake and accumulate greater than 456 mg of cadmium, 3005 mg of lead, or 1195 mg of nickel per kg dry weight of the shoot tissue, as well as 27,043 mg of cadmium, 60,986 mg of lead, or 21,141 mg of nickel per kg dry weight of the root tissue.

TABLE 2

Metal accumulation in shoots and roots of scented geranium (Pelargonium sp. 'Frensham') plants treated with different concentrations of cadmium, lead, and nickel in nitrate form. The shoot and root uptake levels represent average of 2 independent experiments. Concentrations (mg/L) refer to treatment of plants with the described concentrations during 14 day period.

| Heavy Metal | Concentration mg/L | Shoot Uptake mg/kg DW | Root Uptake mg/kg DW |
|---|---|---|---|
| CTL | 0 | 0 | 0 |
| CTL | 0 | 0 | 0 |
| Cd 5 | 250 | 42.38879 | 1716.463 |
| Cd 6 | 500 | 128.8529 | 5492.272 |
| Cd 7 | 750 | 778.42 | 27043.57 |
| Cd 8 | 1000 | 456.9888 | 5125.175 |
| Pb 5 | 1000 | 639.1571 | 38441.85 |
| Pb 6 | 1500 | 520.7667 | 36400.92 |
| Pb 8 | 2000 | 2228.733 | 60986.25 |
| Pb 9 | 2500 | 3005.473 | 40694.12 |
| Ni 5 | 250 | 288.872 | 14998.9 |
| Ni 6 | 500 | 395.0483 | 8086.088 |
| Ni 7 | 750 | 508.051 | 12120.64 |
| Ni 8 | 1000 | 1195.106 | 21141.78 |

EXPERIMENT 6

Scented Geranium Plants and Metal Uptake from Mixture of Metal Contaminants (Cadmium, Lead and Nickel)

Two experiments were conducted with replicate cutting propagated plants of geraniums to assess their ability to uptake and sequester metals in the shoots and roots, when treated with a mixture of cadmium, lead, nickel. In the first experiment, a solution containing 0.8 mg of $CdNO_3$+8.3 mg of $PbNO_3$+5 mg of $NiNO_3$ was used for treating the scented geraniums plants; the metals were provided as cadmium, lead and nickel nitrates dissolved in 250 mL water per plant, applied daily over a 10 days period. In the second experiment, a solution containing higher concentrations of metal mixture (provided as nitrates) was used for treatment, viz., 3.12 mg of $CdNO_3$+31.25 mg of $PbNO_3$+12.5 mg of $NiNO_3$ treatments with these concentrations were repeated daily over a 10 day period; replicates plants were used for each treatment. The overall cadmium, lead and nickel nitrate fed to each plant being for the first experiment: 8 mg Cd, 83 mg Pb, and 50 mg Ni. For the second experiment the total amount fed was 31.2 mg Cd, 312.5 mg Pb and 125 mg Ni. In both experiments the plants were watered with neutral water (pH 7.0). The plants were harvested after 10 days; roots and shoots separated, and dried. Sample preparation consisted of digestion of a known amount of sample following a closed teflon vessel method (Topper, 1990). The samples were analyzed using a Varian Spectra AA Atomic Absorption Spectrophotometer in our laboratory. The data is presented in Table 3.

Based on the results from this experiment (data presented in Table 3), we have observed that scented geranium plants are capable of tolerating a complex mixture of toxic metals and can accumulate a wide variety of metals simultaneously. The treated plants accumulated greater than 207 mg Cd+206 mg Pb+451.5 mg Ni per kg dry weight of the shoot tissue, as well as 1,111 mg Cd+27,803.5 mg Pb+1,385 mg Ni per kg dry weight of the root tissue.

TABLE 3

Metal uptake in Frensham scented geranium plants treated with a mixture of heavy metals (metal mixture composed of lead nitrate, cadmium nitrate and nickel nitrate at different concentrations; Cd3 + Pb3 + Ni3 or Cd9 + Pb9 + Ni9 combinations). The metal uptake values provided are average of 2 plants per treatment. 5 Concentrations (mg/L) refer to treatment of plants with the described concentrations during 10 day period.

| Metal | Concentration mg/L | Metal uptake (Expt.I) mg/kg DW | Metal | Concentration mg/L | Metal uptake (Expt. II) mg/kg DW | Average |
|---|---|---|---|---|---|---|
| Shoots | | | | | | |
| Cd 3 | 10 | 153 | Cd 9 | 25 | 261 | 207 |
| Pb 3 | 100 | 150 | Pb 9 | 250 | 262 | 206 |
| Ni 3 | 40 | 328 | Ni 9 | 100 | 575 | 451.5 |
| Roots | | | | | | |
| Cd 3 | 10 | 913 | Cd 9 | 25 | 1309 | 1111 |
| Pb 3 | 100 | 9760 | Pb 9 | 250 | 45847 | 27803.5 |
| Ni 3 | 40 | 1344 | Ni 9 | 100 | 1427 | 1385.5 |

EXPERIMENT 7
Scented Geranium Plants Tolerance to Cadmium, Lead and Nickel (High Cd, Pb and Ni Concentrations)

Two separate experiments were conducted with replicate cutting propagated plants of Frensham scented geraniums to assess their ability to tolerate varying levels of cadmium, lead and nickel. Five levels of cadmium, lead and nickel were selected for treating the scented geranium: [0, 6.25, 12.5, 18.75, 25 mg of cadmium nitrate; or 0, 25, 37.5, 50, 62.5 mg of lead nitrate; or 0, 6.25, 12.5, 18.75, 25 mg of nickel nitrate dissolved in 50 mL water per plant]. The ability of scented geranium to tolerate excess metal ions, was ascertained by comparing its chlorophyll a fluorescence kinetics to two well established hyperaccumulators namely indian mustard (*Brassica juncea*) and sunflower (*Helianthus annus*). The fluorescence measurements were made on 3 leaf samples, for a total of 9 measurements per treatment per experiment in scented geranium and 2 leaf samples, for a total of 4 measurements per treatment for each indian mustard and sunflower. The Fv/Fm ratio was recorded on the same leaves on alternate days over the 14-day treatment period for scented geranium and up to 7 and 5 days for indian mustard and sunflower, respectively, with a portable fluorometer (Plant Efficiency Analyzer, Hansatech, England). The data is presented below in Table 4.

Based on the results from these experiments (data presented in Table 4), we have observed that Frensham scented geraniums are highly tolerant to cadmium, lead and nickel compared to both indian mustard and sunflower. This was evident from the Fv/Fm ratio, a non-destructive indicator of the metabolic status of plants. The Fv/Fm ratio decreased from 0.82 to 0.43 (after 14 days) in scented geraniums, compared to a decline in the ratio from 0.80 to 0.02 (within 7 days) for indian mustard and 0.81 to 0.03 (within 5 days) for sunflower. These results confirmed that scented geraniums are metabolically active, while indian mustard and sunflower were physiologically restricted at the highest metal levels tested, as an Fv/Fm ratio of less than 0.3 is indicative of senescing and dead tissue.

TABLE 4

Chlorophyll a fluorescence (Fv/Fm ratio) in Frensham scented geraniums, indian mustard and sunflower plants treated with cadmium, lead and nickel for a 14, 7 and 5 days, respectively. (The Fv/Fm ratio are average of 9 measurements for scented geranium and 4 measurements each for indian mustard and sunflower, recorded on alternate days on the same leaves. Ratio was not collected for indian mustard and sunflower beyond 7 and 5 days, respectively because these plants were physiologically dead after these periods)

| | Fv/Fm ratio | | |
|---|---|---|---|
| | Scented geraniums | Indian mustard | Sunflower |
| Cd (1000 mg/L) | | | |
| Day 1 | 0.804 | 0.794625 | 0.8165 |
| Day 3 | 0.769 | 0.580125 | 0.252475 |
| Day 5 | 0.738 | 0.089875 | 0.026 |
| Day 7 | 0.640 | 0.032 | |
| Day 9 | 0.623 | | |
| Day 11 | 0.579 | | |
| Day 13 | 0.553 | | |
| Day 15 | 0.482 | | |
| Pb (2500 mg/L) | | | |
| Day 1 | 0.824 | 0.806625 | 0.808125 |
| Day 3 | 0.813 | 0.523625 | 0.225625 |
| Day 5 | 0.801 | 0.322 | 0.031 |
| Day 7 | 0.758 | 0.03725 | |
| Day 9 | 0.673 | | |
| Day 11 | 0.656 | | |
| Day 13 | 0.591 | | |
| Day 15 | 0.500 | | |
| Ni (1000 mg/L) | | | |
| Day 1 | 0.825 | 0.797375 | 0.82075 |
| Day 3 | 0.774 | 0.348875 | 0.296375 |
| Day 5 | 0.754 | 0.060875 | 0.02625 |
| Day 7 | 0.741 | 0.02125 | |
| Day 9 | 0.663 | | |
| Day 11 | 0.590 | | |
| Day 13 | 0.523 | | |
| Day 15 | 0.429 | | |

EXPERIMENT 8
Pelargonium sp. Grown in Various Media

Different plant growth media, such as different soil types, artificial soil mix, and hydroponics which contain one or more of the metal ions, can be used for growth of scented geraniums. Scented geraniums can be used for both phytoextraction and rhizofiltration processes, based on the growth medium type. In case of soil or artificial soil mixes, the process would be phytoextraction, while using a hydroponic growth medium the process would be a rhizofiltration process. We have successfully grown scented geranium plants in both the soil and the hydroponic systems without any differences in their growth habit, and their metal uptake potential.

Citrosa scented geranium and Frensham scented geranium (Pelargonium sp. 'Citrosa' and Pelargonium sp 'Frensham') plants were planted directly in soils contaminated with low concentrations of lead and copper (the soil also contained hydrocarbon contamination). The levels of contamination were 167.12 ppm of copper and 232.8 ppm of lead, and approximately 40,000 ppm of hydrocarbons. Plants (12 replicates) were harvested on a weekly basis after 2, 3, 4, 5 weeks of growth in the contaminated soils; roots and shoots separated, washed and dried. Sample preparation consisted of digestion of a known amount of sample in a closed teflon vessel method (Topper, 1990). The samples were analyzed using a Varian Spectra AA Atomic Absorption Spectrophotometer in our laboratory.

Based on the results from this experiment (data presented in Table 5), we have observed that scented geranium plants (Frensham and Citrosa scented geraniums) can tolerate a mixture of contamination (heavy metals and hydrocarbons) and they can accumulate greater than 36 mg of copper, 23 mg of lead per kg dry weight of shoot, as well as greater than 35 mg of copper, and 14.9 mg of lead per kg dry weight of the root tissue, under field conditions. Both types of scented geraniums accumulated metal ions (lead and copper) in a linear fashion (metal content in root and shoot increasing with increasing duration of growth in the contaminated soil) even after 5 weeks of growth.

TABLE 5

Metal uptake by scented geranium plants (Pelargonium sp. 'Frensham') grown on contaminated soil containing low-concentrations of lead and copper. The results are average of 12 replicate plants each week starting at week 2 after planting.

| Time (weeks) | Copper (mg/kg DW) | Lead (mg/kg DW) |
| --- | --- | --- |
| Scented geranium shoots | | |
| Week 2 | 19.8 | 12.8 |
| Week 3 | 20.99 | 14.00 |
| Week 4 | 38.66 | 16.73 |
| Week 5 | 36.04 | 23.67 |
| Scented geranium roots | | |
| Week 2 | 12.9 | 9.43 |
| Week 3 | 28.36 | 9.41 |
| Week 4 | 35.94 | 14.42 |
| Week5 | 34.36 | 14.9 |

EXPERIMENT 9
Beauty Oak Scented Geranium Plants and Metal Uptake from Mixture of Metal Contaminants (Lead, Cadmium and Nickel)

An experiment was conducted with replicate cutting-propagated plants of Beauty Oak scented geraniums to assess their ability to uptake and sequester metals in the shoots and roots, when treated with lead, cadmium and nickel, alone and in combination. Solutions containing 50.0 mg of $Pb(NO_3)_2$+10.0 mg of $Cd(NO_3)_2$, and 10.0 mg of $Ni(NO_3)_2$ were used alone and combined for treating the scented geraniums plants; the metals were provided as lead, cadmium and nickel nitrates dissolved in 100 ml of half-strength Hoagland's fertilizer solution (lacking the micronutrients) per plant, applied as needed over a 14 day period. Replicate plants were used for each treatment. The total lead, cadmium and nickel nitrate fed to each plant over the whole treatment period were 350 mg Pb, 70 mg Cd, and 70 mg Ni.

The plants were harvested after 10 days; roots and shoots were separated and dried. Sample preparation consisted of digestion of a known amount of sample following a closed Teflon vessel method (Topper, 1990). The samples were analyzed using a Varian Spectra AA Atomic Absorption Spectrophotometer in our laboratory.

Based on this experiment and data presented in Table 6, we have observed that another variety of Pelargonium sp., Beauty Oak scented geranium plants are capable of tolerating individual as well as a complex mixture of toxic metals and can accumulate a wide variety of metals simultaneously. The treated plants accumulated greater than 65379 mg Pb, 3948 mg Cd and 7350 mg Ni per kg dry weight of root tissue when metals were applied separately, and 68018 mg Pb+48 mg Cd+118 mg Ni per kg dry weight of root tissue when metals were applied in combination.

We also assess other varieties of Pelargonium sp. for their ability to hyperaccumulate metals (Table 7).

TABLE 6

Metal accumulation in shoots and roots of Beauty Oak scented geranium plants treated with concentrations of cadmium, lead, and nickel (in nitrate form) alone and in combination. The shoot and root uptake levels represent an average of 4 replicates per treatment. Concentrations (mg/L) refer to treatment of plants with the described concentrations over a 14 day period. (DW = Dry weight of tissue)

| Heavy Metal (mg/kg DW) | Concentration | Shoot Uptake | |
| --- | --- | --- | --- |
| Control | 0 | 0 | 0 |
| Pb | 500 | 209.4 | 65379.9 |
| Cd | 100 | 17.1 | 3948.1 |
| Ni | 100 | 81.7 | 7350.2 |
| Pb + Cd + Ni | 500 + 100 + 100 | 51.0 + 4.0 + 57.0 | 68018.1 + 48.9 + 118.4 |

TABLE 7

Pelargonium sp. Plant Patents

| Patent No. | Variety Name | Patent No. | Variety Name | Patent No. | Variety Name |
| --- | --- | --- | --- | --- | --- |
| U.S. Pat. No. P007656 | 315-(83-48-1) | U.S. Pat. No. P009534 | BFP-825 Salmon Rose | U.S. Pat. No. P008523 | Designer Salmon |
| U.S. Pat. No. P007620 | Flair | U.S. Pat. No. P009535 | BFP-901 Bright Red | U.S. Pat. No. P008522 | Designer Coral |
| U.S. Pat. No. P007538 | Fantasy | U.S. Pat. No. P009237 | Klehisp | U.S. Pat. No. P008382 | Klepelwa |
| U.S. Pat. No. P007467 | Allure | U.S. Pat. No. P009231 | Pink Pearl | U.S. Pat. No. P008296 | BSR-100B Dark Salmon cultivar |

TABLE 7-continued

Pelargonium sp. Plant Patents

| Patent No. | Variety Name | Patent No. | Variety Name | Patent No. | Variety Name |
|---|---|---|---|---|---|
| U.S. Pat. No. P007387 | Majestic | U.S. Pat. No. P009228 | BFP-445 Salmon | U.S. Pat. No. P008288 | BSR-233 Bright Coral cultivar |
| U.S. Pat. No. P007343 | Crystal | U.S. Pat. No. P009230 | BFP-285 Pink Parfait | U.S. Pat. No. P008287 | BSR-284 Pink cultivar |
| U.S. Pat. No. P010396 | Pink Passion | U.S. Pat. No. P009229 | Starburst Red | U.S. Pat. No. P008286 | BSR-194 Cherry cultivar |
| U.S. Pat. No. P010139 | Sunrise | U.S. Pat. No. P009217 | BFP-721 Bright Lilac | U.S. Pat. No. P008285 | BSR-232 Light Scarlet cultivar |
| U.S. Pat. No. P010399 | BFP-1328 Red | U.S. Pat. No. P009219 | BFP-420 Bright Red | U.S. Pat. No. P008284 | BSR-177 White cultivar |
| U.S. Pat. No. P010395 | Purple Rose | U.S. Pat. No. P009218 | Pink Heart | U.S. Pat. No. P008089 | Jubilee |
| U.S. Pat. No. P010398 | BFP-484 White | U.S. Pat. No. P009215 | Klespri | U.S. Pat. No. P007627 | 208 (81-344-3) |
| U.S. Pat. No. P010397 | BFP-1409 Light Salmon | U.S. Pat. No. P009216 | Kleirro | U.S. Pat. No. P007576 | Centennial |
| U.S. Pat. No. P009596 | BFP-790 Pink Parfait | U.S. Pat. No. P009204 | Klegoes | U.S. Pat. No. P007351 | 821-(82-116-13) |
| U.S. Pat. No. P009589 | BFP-864 Bright Lavender | U.S. Pat. No. P009206 | Klevette | U.S. Pat. No. P006761 | Serenade |
| U.S. Pat. No. P009590 | BFP-873 Bright Red | U.S. Pat. No. P009205 | Klemiga | U.S. Pat. No. P006717 | Feeling |
| U.S. Pat. No. P009580 | BFP-837 Scarlet | U.S. Pat. No. P008669 | Designer Scarlet | U.S. Pat. No. P010606 | Guilan |
| U.S. Pat. No. P009560 | BFP-817 Light Salmon | U.S. Pat. No. P008552 | Designer Light Pink | U.S. Pat. No. P009287 | L'amour |
| U.S. Pat. No. P009551 | BFP-788 Bright Scarlet | U.S. Pat. No. P008521 | Showcase Red | U.S. Pat. No. P004785 | Geranium plant |
| U.S. Pat. No. P009552 | Lilac Chiffon | U.S. Pat. No. P008525 | Designer Hot Pink | U.S. Pat. No. P004778 | Geranium plant |
| U.S. Pat. No. P009544 | BFP-838 Dark Red | U.S. Pat. No. P008524 | Designer Rose | / | / |

Based on the findings reported here, along with an extensive comparison with published literature on other hyperaccumulators, we have concluded that Scented geraniums (Pelargonium sp.) are hyperaccumulators of heavy metals (lead, cadmium, copper, nickel, chromium etc.) and can be used for phytoremediation of metal-tainted soils. The data obtained so far utilizing this process satisfies the EPA's (US Environmental Protection Agency) set goal for metal hyperaccumulators, which is ".... absorb, translocate and tolerate levels of metals in the 0.1 to 1.0 percent range....".

All publications, patents and patent applications are herein incorporated by reference in their entirety to the same extent as if each individual publication, patent or patent application was specifically and individually indicated to be incorporated by reference in its entirety.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

We claim:

1. A method for removing one or more species of metal from a growth medium, comprising growing a Pelargonium sp. scented geranium plant in the growth medium for a time period sufficient for the plant root to uptake and hyperaccumulate metal in the root or shoot biomass, wherein the metal is selected from one or more members of the group consisting of lead, cadmium, copper, nickel and zinc.

2. A method according to claim 1, wherein the Pelargonium sp. plant is selected from the group consisting of Pelargonium sp. 'Frensham', Pelargonium sp 'Citrosa' and Pelargonium sp 'Beauty Oak'.

3. A method according to claim 2, wherein the Pelargonium sp. plant is selected from the group consisting of Pelargonium sp. 'Frensham', and Pelargonium sp 'Beauty Oak'.

4. A method according to claim 3, wherein the Pelargonium sp. plant is Pelargonium sp. 'Frensham'.

5. A method according to claim 1, wherein the growth medium comprises solid medium, semi-solid medium, liquid medium or a combination thereof.

6. A method according to claim 5, wherein the growth medium comprises soil, sand, sludge, compost, or artificial soil mix.

7. A method according to claim 5, wherein the growth medium comprises organic contaminants selected from the group consisting of petroleum industry by-products and petroleum industry wastes.

8. A method according to claim 1, wherein the metal comprises cadmium accumulated at a concentration of about 450 mg Cd/kg to 27,500 mg Cd/kg dry weight of the plant.

9. A method according to claim 1, wherein the metal comprises lead accumulated at a concentration of about 1,300 mg Pb/kg to 70,000 mg Pb/kg dry weight of the plant.

10. A method according to claim 1, wherein the metal comprises nickel accumulated at a concentration of about 400 mg Ni/kg to 21,500 mg Ni/kg dry weight of the plant.

11. The method of claim 1, further comprising the step of harvesting one or more parts of the plant, the part being selected from the group consisting of a portion of the root biomass, a portion of the shoot biomass, the entire root biomass, the entire shoot biomass and the entire root and shoot biomass.

12. A method according to claim 11, wherein the portion of the shoot biomass comprises a leaf or a stem.

13. A method according to claim 11, wherein a sufficient portion of the shoot biomass is not harvested to permit continued plant growth.

14. A method according to claim 1, further comprising the steps of harvesting one or more parts of the plant, the part being selected from the group consisting of a portion of the root biomass, a portion of the shoot biomass the entire root biomass, the entire shoot biomass and the entire root and shoot biomass, and extracting essential aromatic oil from the root or shoot biomass.

15. A method according to claim 14, wherein essential aromatic oil is obtained by distillation.

16. A method according to claim 15, wherein the essential aromatic oil is selected from the group consisting of citronellol, geraniol, iso-methane and geranyl formate.

17. The method of claim 1, wherein one or more parts of the plant selected from the root and shoot biomass is harvested and metal in the root or shoot biomass is concentrated.

18. A method according to claim 17, wherein concentration of metal is carried out by a method selected from the group consisting of air drying, dehydrating, ashing, incineration, smelting, aerobic digestion and anaerobic digestion of the residual oil-extracted shoot biomass.

* * * * *